US00PP11743P2

(12) United States Plant Patent
Bullis

(10) Patent No.: US PP11,743 P2
(45) Date of Patent: Jan. 16, 2001

(54) AECHMEA PLANT NAMED 'BLUE TANGO'

(75) Inventor: Patricia Elena Gomez Bullis, Princeton, FL (US)

(73) Assignee: Bullis Bromeltads, Inc., Princeton, FL (US)

( * ) Notice: Under 35 U.S.C. 154(b), the term of this patent shall be extended for 0 days.

(21) Appl. No.: 09/291,100

(22) Filed: Apr. 14, 1999

(51) Int. Cl.[7] ..... A01H 5/00
(52) U.S. Cl. ..... Plt./370

(58) Field of Search ..... Plt./370

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Aechmea named 'Blue Tango' particularly characterized by its upright and outwardly arching plant habit; rapid growth rate; strong and erect scapes; tightly branched inflorescences with bluish purple flower bracts and sepals; fuchsia red scapes; and long-lasting inflorescences.

1 Drawing Sheet

BACKGROUND OF THE INVENTION

The present invention relates to a new and distinct cultivar of Aechmea plant, botanically known as *Aechmea dichlamydea trinitensis*×*A. fendleri*, and hereinafter referred to by the cultivar name Blue Tango.

The new Aechmea is a product of a planned breeding program conducted by the Inventor in Princeton, Fla. The objective of the breeding program was to develop blue-flowered Aechmeas.

The new Aechmea originated from a cross made in Princeton, Fla. by the Inventor of an unnamed selection of *Aechmea dichlamydea trinitensis* as the female, or seed, parent with an unnamed selection of *Aechmea fendleri* as the male, or pollen, parent. The cultivar Blue Tango was discovered and selected by the Inventor in April, 1994, as a seedling within the progeny of the stated cross in a controlled environment in Princeton, Fla.

Plants of the new Aechmea differ from plants of the female parent primarily in flower bract and sepal color. In addition, plants of the new Aechmea have much more compact inflorescence form than plants of the female parent.

Plants of the new Aechmea differ from plants of the male parent in plant size, leaf width and inflorescence branching. In addition, plants of the new Aechmea maintain inflorescence color much longer than plants of the male parent.

Asexual propagation of the new cultivar by offsets and by tissue culture at Princeton, Fla. has shown that the unique features of this new Aechmea plant are stable and reproduced true to type in successive generations.

SUMMARY OF THE INVENTION

The new Aechmea has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Blue Tango'. These characteristics in combination distinguish 'Blue Tango' as a new and distinct cultivar:

1. Plants of the new Aechmea are upright and outwardly arching in plant habit.

2. Plants of the new Aechmea have a rapid growth rate.

3. Inflorescences of the new Aechmea are held upright on strong and erect fuchsia red scapes.

4. Plants of the new Aechmea have tightly branched inflorescences with bluish purple flower bracts and sepals.

5. Inflorescences of the new Aechmea are very long-lasting; typically color will be maintained for about five to seven months.

6. Dried inflorescences, although persistent, do not detract from the new Aechmea's overall appeal.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprses a side perspective view of a typical plant of 'Blue Tango' about one-year old and grown in a 15-cm container.

The photograph at the bottom of the sheet comprises a close-up view of a typical inflorescence of 'Blue Tango'. Leaf and inflorescence colors in the photographs may appear different from the actual colors due to light reflectance.

DETAILED BOTANICAL DESCRIPTION

The following observations, measurements and comparisons describe plants that were about one-year old and grown in 15-cm containers in Princeton, Fla., under a polypropylene-covered shadehouse and conditions which closely approximate those used in horticultural practice. Plants were grown under day temperatures ranging from 24 to 35° C. and night temperatures ranging from 16 to 21° C. The polypropylene shade provided a 70 percent decrease in ambient light level. In the following description, color references are made to The Royal Horticultural Society Colour Chart except where general terms of ordinary dictionary significance are used.

Botanical classification: *Aechmea dichlamydea trinitensis*× *A. fendleri* cultivar Blue Tango.

Parentage:

*Female, or seed, parent.*—Unnamed selection of *Aechmea dichlamydea trinitensis.*

*Male, or pollen, parent.*—Unnamed selection of *Aechmea fendleri.*

Propagation:

*Type.*—By offsets and by tissue culture.

*Time to initiate roots.*—Summer: About 30 days at 29 to 35° C. Winter: About 60 days at 18 to 24° C.

*Time to develop roots.*—Summer: About 60 days at 29 to 35° C. Winter: About 100 days at 18 to 24° C.

*Rooting habit.*—Fine, freely branching.

Plant description:

*Plant shape.*—Upright and outwardly arching.

*Growth habit.*—Erect when young, becoming outwardly arching with development. Appropriate for 12.5 to 25.5-cm containers. Plants readily produce offsets.

*Crop time.*—About 12 months are required to produce a finished plant in a 20-cm container and about 18 months are required to produce a finished plant in a 25.5-cm container.

*Plant size.*—Height, soil surface to top of leaf canopy: About 80 cm. Width: About 85 cm.

*Plant vigor.*—Moderate, rapid growth rate.

*Foliage description.*—Arrangement: Rosette, spiral phyllotaxis. Quantity of leaves per plant: About 12 to 15. Shape: Linear. Length, fully expanded: About 64 cm. Width, fully expanded: About 5 cm. Margin: Spiny. Apex: Acuminate to aristate. Aspect: Concave. Texture: Leathery, stiff, smooth, glabrous, waxy, glossy. Leaf Sheath: Not observed. Color: Young and mature, upper surface: 144A. Young and mature, lower surface: 144A.

Inflorescence description:

*Inflorescence form.*—Large terminal inflorescences arranged in tightly branched tri-lateral panicles supported by erect and strong scapes. Each lateral panicle with about 12 to 15 individual flowers. Flowers ovoid in shape; bluish purple sepals and flower bracts.

*Inflorescence longevity.*—Inflorescences of the new Aechmea are very long-lasting, typically color will be maintained for about five to seven months. Dried inflorescences, although persistent, do not detract from the new Aechmea's overall appeal.

*Inflorescence length.*—From lowest panicle to uppermost panicle apex, about 45 cm.

*Inflorescence width.*—About 18.5 cm.

*Flower height.*—About 1.6 cm.

*Flower diameter.*—About 5 mm.

*Primary bracts.*—Arrangement: Subtend each tri-lateral panicles. Shape: Linear. Texture: Papery, smooth. Color: Initially red, 53B, then becoming tan, 164A to 164B, when dry.

*Flower bracts.*—Arrangement: Closely adhered to sepals. Shape: Elongate, sharply acuminate. Length: About 2 cm. Width: About 1 cm. Texture: Smooth. Color: Base: 74A. Apex: 93A to 93C.

*Sepals.*—Shape: Elongate, apiculate. Length: About 1.6 cm. Width: About 6 mm. Color: Base: White, close to 155D, to light green, 144C to 144B. Mid-section: Close to 74A. Apex: Close to 93A to 93B fading to close to 89C.

*Petals.*—Not united, usually with two scales inside of sepals. Color: White to green, 154A.

*Time to flower.*—About 4 to 6 weeks after sticking and offset.

*Natural flowering time.*—Summer.

*Scape.*—Length: About 52 cm. Diameter: About 1.3 cm. Texture: Smooth. Color: 53B.

*Lateral flowering stems* (*lowest terminal panicle*).—Length: About 4.1 cm. Diameter: About 6 mm. Texture: Smooth. Color: 53B.

*Reproductive organs.*—Minute, inconspicuous, greenish white in color.

Disease resistance: Resistance to pathogens common to Aechmeas has not been noted.

Seed production: Seed production has not been observed.

It is claimed:

1. A new and distinct cultivar of Aechmea plant named 'Blue Tango', as illustrated and described.

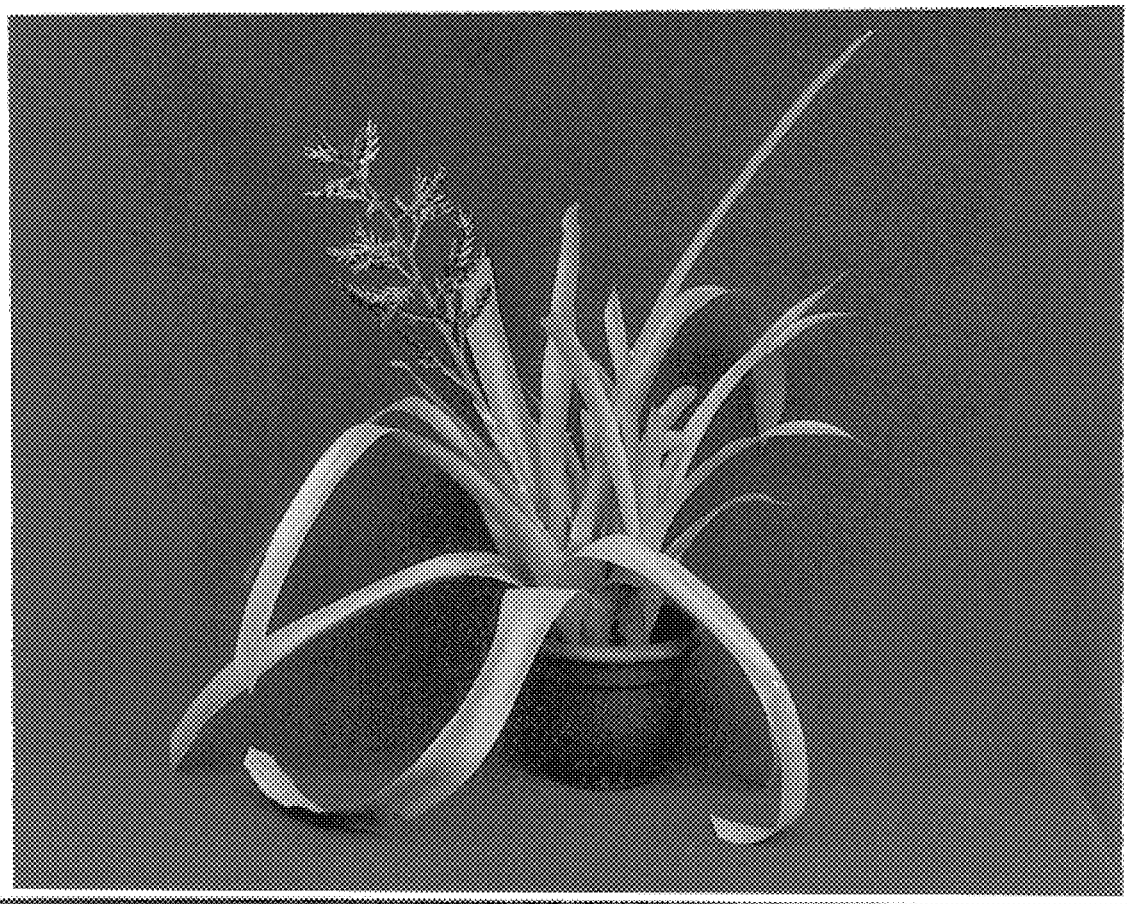
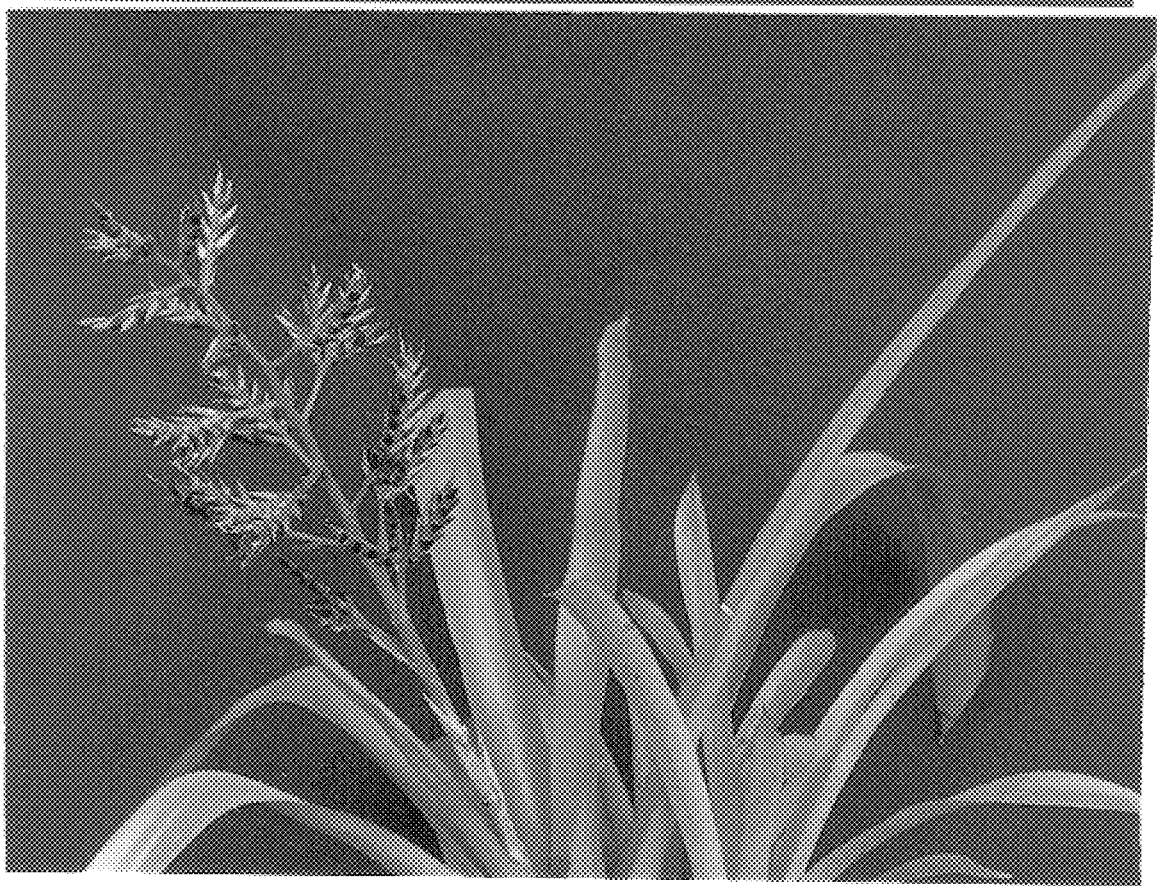

* * * * *